United States Patent [19]

Richards

[11] Patent Number: 4,985,418

[45] Date of Patent: Jan. 15, 1991

[54] PHARMACEUTICAL COMPOSITIONS

[75] Inventor: David A. Richards, Cambridge, United Kingdom

[73] Assignee: Glaxo Group Limited, England

[21] Appl. No.: 137,169

[22] Filed: Dec. 23, 1987

[30] Foreign Application Priority Data

Dec. 24, 1986 [GB] United Kingdom ............... 8630913

[51] Int. Cl.$^5$ .............................................. A61K 31/56
[52] U.S. Cl. .................................... 514/179; 514/180
[58] Field of Search ............................... 514/179, 180

[56] References Cited

U.S. PATENT DOCUMENTS

| | | | |
|---|---|---|---|
| 4,335,121 | 6/1982 | Phillips et al. | 514/179 |
| 4,578,221 | 3/1986 | Phillips et al. | 260/397.1 |
| 4,650,610 | 3/1987 | Phillips et al. | 260/397.1 |
| 4,710,495 | 12/1987 | Bodor | 514/174 |

Primary Examiner—H. M. S. Sneed
Assistant Examiner—James Saba
Attorney, Agent, or Firm—Bacon & Thomas

[57] ABSTRACT

Use of fluticasone propionate in the treatment of bowel diseases when administered by the oral, stomal or rectal routes.

8 Claims, No Drawings

PHARMACEUTICAL COMPOSITIONS

This invention relates to pharmaceutical compositions for use in the treatment of inflammatory bowel diseases and other bowel diseases which respond to treatment with glucocorticoid steroids, for example celiac disease.

Inflammatory bowel disease is the term generally applied to two diseases, namely ulcerative colitis and Crohn's disease.

Ulcerative colitis is a chronic inflammatory disease of unknown aetiology afflicting only the large bowel and, except when very severe, limited to the bowel mucosa. The course of the disease may be continuous or relapsing, mild or severe. It is curable by total colectomy which may be needed for acute severe disease or chronic unremitting disease. Most patients with ulcerative colitis are managed medically rather than surgically.

Crohn's disease is also a chronic inflammatory disease of unknown aetiology but, unlike ulcerative colitis, it can affect any part of the bowel. Although lesions may start superficially, the inflammatory process extends through the bowel wall to the draining lymph nodes. As with ulcerative colitis, the course of the disease may be continuous or relapsing, mild or severe but, unlike ulcerative colitis it is not curable by resection of the involved segment of bowel. Most patients with Crohn's disease come to surgery at some time, but subsequent relapse is common and continuous medical treatment is usual.

For treatment of acute attacks of ulcerative colitis, glucocorticoid steroids such as prednisone or prednisolone acetate are almost invariably used and given by mouth for the average acute attack or relapse, or locally, by enema.

After remission has been achieved, sulphasalazine is the maintenance treatment of choice in treating ulcerative colitis. This drug, however, has a significant number of side effects chiefly due to absorption of the sulphapyridine moiety from the colon. Recently compounds which contain only 5-amino-salicylic acid have been developed; these are as effective as sulphasalazine and do not have the sulphapyridine side effects but do have side effects of their own, notably diarrhoea.

Glucocorticoid steriods are, however, not used for maintenance of remission in ulcerative colitis; doses that do not produce unacceptable side effects are ineffective, and patients who need chronic high dose glucocorticoid steroids for control of their disease almost invariably are treated by colectomy.

As with ulcerative colitis, glucocorticoid steroids are the treatment of choice for severe active Crohn's disease, but ideally only to achieve remission, after which they should be stopped. However, all too frequently the disease does not satisfactorily remit, and glucocorticoid steroids may be necessary to maintain control of symptoms. Sulphasalazine is also useful in less severe cases, particularly for disease involving the colon.

Very often in Crohn's disease, however, primary medical treatment of the disease process is ineffective, and only symptomatic treatment is of value i.e. analgesics for pain and opiates for diarrhoea. Most patients eventually require surgery.

Celiac disease is a chronic intestinal disorder caused by a specific intolerance to gluten present in wheat and rye proteins leading to changes in the small intestinal mucosa and impaired absorption. Current treatment is effected by a well balanced gluten-gliadin free diet high in calories and proteins and normal in fat. This excludes cereal grains with the exception of rice and corn. Those patients with celiac disease who do not respond to the glutengliaden free diet are given glucocorticoid steroids such as hydrocortisone, prednisone or prednisolone.

Our studies indicate that these diseases may advantageously be treated using the anti-inflammatory steroid S-fluoromethyl $6\alpha$, $9\beta$-difluoro-$11\beta$-hydroxy-$16\alpha$-methyl-$17\alpha$-propionyloxy-3-oxoandrosta-1,4-diene-$17\beta$-carbothioate, which has the approved name "fluticasone propionate".

Fluticasone propionate is described and claimed in United Kingdom Patent Specification 2088877B and shows good anti-inflammatory activity on topical application and may be used in anti-inflammatory therapy, for example, by topical application to the skin, for the treatment of inflammatory dermatoses of humans and animals, for example eczema, which are normally responsive to glucocorticoid steroid therapy, and also of less responsive conditions such as psoriasis in humans.

The above United Kingdom Patent Specification also indicates that the active glucocorticoid steroids, which include fluticasone propionate, may in general be given by internal administration, including oral or rectal administration; however this is only in the context of cases where systemic adrenocortical therapy is indicated. There is no suggestion that the active glucocorticoid steroids would be of use in treating inflammatory diseases of the bowel or other bowel diseases such as celiac disease.

We have surprisingly found that fluticasone propionate, unlike other glucocorticoid steroids used in the treatment of inflammatory bowel disease and contrary to the teaching of the above United Kingdom patent specification, is poorly absorbed from the gastrointestinal tract; furthermore it appears to be rapidly metabolised even when absorbed and its systemic effects from the oral route are negligible.

These advantageous properties are of great potential benefit in the treatment of inflammatory bowel disease. Thus, it is possible for the drug to reach the inflamed site in the bowel in sufficient concentration to exert direct anti-inflammatory therapeutic action for a relatively long time with the possibility of systemic side effects being greatly reduced or even eliminated.

Fluticasone propionate thus potentially represents a very significant advance over other glucocorticoid steroids which exert their effects systemically and other drugs previously used for the management of Crohn's disease and celiac disease, particularly in avoiding the systemic side effects normally associated with glucocorticoid steroid therapy. The virtual non-absorption of the drug renders possible its safe use in the maintenance therapy of the disease as well as achieving remission in the acute phase. Although Crohn's disease is not a very common condition, it is a chronic and often debilitating disorder that can benefit from a safer and more effective treatment.

In ulcerative colitis, fluticasone propionate may help to reduce the number of patients having to undergo surgery and in addition, its lack of systemic effects makes it possible to use the drug for maintenance therapy once remission has been achieved.

The invention therefore provides pharmaceutical compositions comprising fluticasone propionate for use in the treatment by the oral, stomal or rectal route of bowel diseases which respond to treatment with glucocorticoid steroids.

The invention also provides the use of fluticasone propionate in the preparation of pharmaceutical compositions for the treatment by the oral, stomal or rectal route of bowel diseases which respond to treatment with glucocorticoid steroids.

The invention further provides a method of treatment of bowel diseases which respond to treatment with glucocorticoid steroids wherein an effective dose of fluticasone propionate is administered by the oral, stomal or rectal route to a human or animal subject suffering from said bowel disease responsive to glucocorticoid steroids.

The invention is particularly applicable to inflammatory bowel disease as hereinbefore defined, and celiac disease.

For oral administration, the pharmaceutical composition can be in the form of suspensions, capsules or tablets, and can be formulated by conventional methods. Ideally, in ulcerative colitis, fluticasone propionate should be formulated so that it is released preferentially in the colon. Alternatively, in Crohn's disease fluticasone propionate may also be formulated so that it is released preferentially in the upper small bowel or stomach.

The most preferred compositions are slow, delayed or positioned release tablets or capsules, in particular tablets or capsules having an enteric coating, that is a coating resistant to conditions within the stomach but releasing the contents in the colon. Such formulations are novel, and constitute a further feature of the invention; any previous disclosure of oral formulations of fluticasone propionate, for example in our above United Kingdom Patent Specification, have been in the context of systemic anti-inflammatory activity and there has been no previous proposal to formulate fluticasone propionate in delayed release, positioned release or enteric coated tablets. These would not, of course, have been thought necessary or desirable merely for systemic absorption.

Suitable compositions for delayed release or enteric coated oral formulations include tablet formulations film coated with materials that are water resistant, pH sensitive, digested or emulsified by intestinal juices or sloughed off at a slow but regular rate when moistened. Examples of suitable coating materials are combinations of hydroxypropyl methylcellulose and ethyl cellulose, cellulose acetate phthalate; polyvinyl acetate phthalate; hydroxypropyl methylcellulose phthalate; polymers of methacrylic acid and its esters. These coating materials may be used alone or in combination to achieve the required release characteristics. Plasticisers such as polyethylene glycol, dibutylphthalate, triacetin and castor oil may be used. A pigment may also be used to colour the film.

Alternatively, materials may be incorporated into the matrix of the tablet e.g. hydroxypropyl methylcellulose; ethyl cellulose or polymers of acrylic and methacrylic acid esters. These latter materials may also be applied to tablets by compression coating.

The dosage range for treatment of inflammatory bowel disease and celiac disease is suitably 2–40 mg per day, preferably 10–30 mg per day for adults and 2–15 mg per day for children.

A convenient daily dose by the oral route would be of the order of 2mg to 20mg per day, depending on the condition of the patient, advantageously in the form of dosage units containing from 1 mg to 10mg per dosage unit, preferably 1 mg to 5mg per dosage unit. A convenient regimen in the case of a slow release, delayed release or positioned release tablet would be 1,2,3 or 4 times a day depending on the condition of the patient. In the acute phase, the daily dosage may preferably be in the range 10mg to 20mg per day, while for maintenance therapy, the daily dose may preferably be in the range 2mg to 10mg per day.

The pharmaceutical composition could also be in a form suitable for stomal or rectal administration for example as an enema in a suitable buffered aqueous vehicle, or as suppositories prepared for example with commercial suppository bases. In the case of stomal or rectal administration the daily dose would be of the order of 2mg to 15mg per day, preferably 10mg to 15mg per day for the acute phase and 2mg to 10mg per day for maintenance therapy.

The following pharmaceutical compositions comprising fluticasone propionate can be used in the treatment of bowel diseases according to the invention.

EXAMPLE 1

Tablets for Oral Administration

Tablets may be prepared by the normal methods such as direct compression or wet granulation.

| Tablet | mg/tablet |
| --- | --- |
| Fluticasone propionate (micronised) | 5.0 |
| Lactose* | 92.5 |
| Croscarmellose Sodium | 2.0 |
| Magnesium Stearate | 0.5 |
| Compression weight | 100.0 |

*of a grade suitable for direct compression

The active ingredient is blended with the lactose, croscarmellose sodium and magnesium stearate. The resultant mix is compressed into tablets using 5.5 mm diameter punches. Tablets of other strengths may be prepared by altering the ratio of active ingredient to lactose or the compression weight and using punches to suit. The tablets are film coated with the following film coating suspension using suitable film coating equipment to give a weight of film coat of approximatly 5 mg.

|  | % w/w |
| --- | --- |
| Eudragit L30D** | 50.0 |
| Propylene glycol | 1.5 |
| Talc | 3.5 |
| Silicone emulsion (antifoam) | 0.1 |
| Purified Water to | 100.0 |
| Polymer content | 15% |
| Total solids | 20% |

**A proprietary aqueous film coating material consisting of a 30% w/w dispersion of a copolymer of polymethacrylic acid and acrylic acid esters obtained from Rohm Pharma.

EXAMPLE 2

Suspensions for Oral Administration (a) Formulation for extemporaneous Preparation on a Daily Basis

| Formula | % W/V |
| --- | --- |
| Fluticasone propionate (micronised) | 0.105* |
| Polysorbate 80 | 0.010 |
| Sodium Saccharin | 0.300 |

| Formula | % W/V |
|---|---|
| Sodium chloride | 0.200 |
| Purified water to | 100.000 |

*includes a 5% overage

Method of preparation

Slurry the fluticasone propionate in a solution of polysorbate 80 in a small proportion of the water. Dissolve the sodium saccharin and sodium chloride in the bulk of the water. Add the fluticasone propionate slurry to the bulk solution and mix. Make up to volume with water and mix.

Dosage 5 mls or multiples thereof.

(b) Ready Prepared Formulations

| (i) Formula | % W/W |
|---|---|
| Fluticasone propionate (micronised) | 0.10 |
| Avicel RC 591** | 1.00 |
| Methyl p-hydroxy benzoate | 0.12 |
| Propyl p-hydroxybenzoate | 0.03 |
| Sodium saccharin | 0.3 |
| Sodium chloride | 0.2 |
| Disodium hydrogen phosphate | 0.06 |
| Citric acid | 0.05 |
| Polysorbate 80 | 0.01 |
| Purified water to | 100.00 |

**[microcrystalline cellulose plus sodium carboxymethyl cellulose]

Method of preparation

Slurry the fluticasone propionate in a solution of the polysorbate 80 in a small proportion of the water. Disperse the Avicel in about 20% of the water. Heat the bulk of the water to 70° C., add and dissolve the p-hydroxy benzoates. Add and dissolve the disodium hydrogen phosphate, citric acid, sodium saccharin and sodium chloride, cool, add the Avicel dispersion followed by the fluticasone propionate slurry. Mix and make up to volume with water.

(ii) As, (i) substituting benzoic acid 0.1% for the p-hydroxybenzoates.

EXAMPLE 3

| Formula | % W/W |
|---|---|
| Fluticasone propionate (micronised) | 0.01 |
| Methyl-p-hydroxybenzoate | 0.12 |
| Propyl p-hydroxybenzoate | 0.03 |
| Disodium hydrogen phosphate | 0.06 |
| Citric acid | 0.05 |
| Cetostearyl alcohol | 0.65 |
| Cetomacrogol 1000 | 1.00 |
| Liquid paraffin | 1.50 |
| Purified water to | 100.00 |

Method of preparation

Heat most of the water to 75° C., dissolve the phydroxybenzoates followed by the disodium hydrogen phosphate and citric acid. Melt together the cetostearyl alcohol, most of the cetomacrogol and the liquid paraffin, heating the mixture to 70° C. Add this mixture to the hot aqueous phase (70° to 75° C.), stir and cool to 50° C.

Slurry the fluticasone propionate in a small proportion of the water containing a small portion of the cetomacrogol. Add the slurry to the bulk with stirring while the latter is at 50° C. Continue stirring while cooling until a temperature of 35° C. is reached.

Fill 100 ml aliquots into bottles or enema bags.

What is claimed is:

1. A pharmaceutical composition comprising an effective amount of fluticasone propionate to treat bowel disease in a human or animal subject in tablet or capsule from, characterized in that said tablet or capsule has an enteric coating.

2. A pharmacuetical composition according to claim 1 wherein the effective amount is from 2 to 40 mg per day.

3. A method of treatment of ulcerative colitis, Crohn's disease or celiac disease comprising adminsitering an effective dose of fluticasone propionate by the oral, stomal or rectal route of a human or animal subject suffering from said ulcerative colitis, Crohn's disease or celiac disease.

4. A method as claimed in claim 3 wherein the fluticasone propionate is administered in a dosage range of from 2 to 40 mg per day.

5. A method as claimed in claim 3 wherein the fluticasone propionate is administered from 1 to 4 times per day in slow release, delayed release or positioned release form.

6. A method as claimed in claim 5 wherein the fluticasone propionate is in enteric coated form.

7. A method as claimed in claim 3 which provides direct anti-inflammatory therapeutic action and greatly reduces systematic side effects.

8. A method as claimed in claim 3 wherein the disease is Crohn's disease or celiac disease and the method is maintenance therapy.

* * * * *

UNITED STATES PATENT AND TRADEMARK OFFICE
CERTIFICATE OF CORRECTION

PATENT NO. : 4,985,418
DATED : January 15, 1991
INVENTOR(S) : David A. Richards

It is certified that error appears in the above-identified patent and that said Letters Patent is hereby corrected as shown below:

COLUMN 6;

Claim 1, line 4, change "from" to --form--.

Claim 2, line 1, change "pharmacuetical" to --pharmaceutical--.

Claim 3, beginning at the end of line 2, change "adminsitering" to --administering--.

Claim 7, line 3, change "systematic" to --systemic--.

Signed and Sealed this

Seventh Day of July, 1992

Attest:

DOUGLAS B. COMER

Attesting Officer  Acting Commissioner of Patents and Trademarks